(12) United States Patent
Yadav et al.

(10) Patent No.: US 8,968,780 B2
(45) Date of Patent: Mar. 3, 2015

(54) STABILIZED PHARMACEUTICAL COMPOSITION

(75) Inventors: Kamala S. Yadav, Mumbai (IN); Amita P. Surana, Thane (IN); Sanjivani A. Kulkarni, Mumbai (IN); Rashmi R. Prasade, Thane (IN)

(73) Assignee: Egis Gyogyszergyar Nyilvanosan Muekoedoe Reszvenytarsasag, Budapest (HU)

( * ) Notice: Subject to any disclaimer, the term of this patent is extended or adjusted under 35 U.S.C. 154(b) by 0 days.

(21) Appl. No.: 13/582,162

(22) PCT Filed: Mar. 1, 2011

(86) PCT No.: PCT/HU2011/000019
§ 371 (c)(1),
(2), (4) Date: Nov. 1, 2012

(87) PCT Pub. No.: WO2011/107812
PCT Pub. Date: Sep. 9, 2011

(65) Prior Publication Data
US 2013/0064893 A1    Mar. 14, 2013

(30) Foreign Application Priority Data
Mar. 1, 2010  (HU) ..................... 1000120

(51) Int. Cl.
*A61K 9/28* (2006.01)
*A61K 9/16* (2006.01)
*A61K 31/197* (2006.01)

(52) U.S. Cl.
CPC ............. *A61K 9/1623* (2013.01); *A61K 31/197* (2013.01)

USPC .......................................................... 424/474

(58) Field of Classification Search
None
See application file for complete search history.

(56) References Cited

U.S. PATENT DOCUMENTS

| 2007/0269511 A1* | 11/2007 | Bockbrader et al. .......... 424/468 |
| 2008/0058420 A1 | 3/2008 | Rampoldi et al. |
| 2010/0255067 A1 | 10/2010 | Sammohi et al. |

FOREIGN PATENT DOCUMENTS

| WO | WO 02/078747 | 10/2002 |
| WO | WO 03/080588 | 10/2003 |
| WO | WO 2006008295 | * 1/2006 |
| WO | WO 2007/107835 | 9/2007 |
| WO | WO 2007107835 | * 9/2007 |

OTHER PUBLICATIONS

Rowe et al; Handbook of Pharm. Excipients; AphA Pubs, 6$^{th}$ Edition; 2009; 414-415; 342-346.
Cutrignelli et al; Comparative effects of some . . . ; Int. Journ. Pharm. 332; 2007; 98-106.

* cited by examiner

*Primary Examiner* — Snigdha Maewall
(74) *Attorney, Agent, or Firm* — Lucas & Mercanti, LLP; Jonathan Myers

(57) ABSTRACT

The invention relates to stabilized pharmaceutical composition comprising pregabalin and a disaccharide or higher polyol as stabilizer and optionally a conventional pharmaceutically acceptable carrier. The stabilized pharmaceutical composition according to the invention is useful in the treatment of a number of diseases such as epilepsy, Alzheimer's disease or Parkinson's disease.

4 Claims, No Drawings

STABILIZED PHARMACEUTICAL COMPOSITION

FIELD OF THE INVENTION

The present invention relates to a stabilized pharmaceutical composition of gamma aminobutyric acid ("GABA") analog, and a process for the preparation of the same. Particularly, the invention relates to a stabilized pharmaceutical composition comprising a GABA analog and a disaccharide or higher polyol as a stabilizer.

TECHNICAL BACKGROUND OF THE INVENTION

Gamma aminobutyric acid ("GABA") is a principal inhibitory neurotransmitter in the central nervous system of mammals. GABA regulates neuronal excitability by binding to specific transmembrane receptors ($Cl^-$-channel-coupled $GABA_A$ receptors and G-protein-coupled $GABA_B$ receptors) resulting in stabilization or hyperpolarization of the resting membrane potential. Attenuation of GABAergic neurotransmission is involved in the pathophysiology of several central nervous system disorders in humans, namely anxiety, epileptic seizures, movement disorders, panic, depression, alcoholism, pain and manic behavior. Numerous GABA analogs have therefore been synthesized and described in the art. Amongst the synthesized GABA analogs, gabapentin, pregabalin, vigabatrin and baclofen have been marketed and used for the treatment of different disorders.

5-methyl-3-aminomethyl-hexanoic acid, called pregabalin, is an analog of GABA that decreases central neuronal excitability by binding to an auxiliary alpha-2-delta subunit of a voltage-gated calcium channel on neurons in the central nervous system. Pregabalin, disclosed in U.S. Pat. Nos. 5,563,175 and 6,197,819, marketed under the name LYRICA® in the U.S. is used in the treatment of peripheral neuropathic pain, epilepsy and generalized anxiety disorder. Pregabalin is also effective at treating chronic pain in disorders such as fibromyalgia and spinal cord injury. U.S. Pat. No. 6,117,906 discloses the use of pregabalin in treating anxiety; U.S. Pat. No. 6,001,876 discloses the use of pregabalin in treating pain; U.S. Pat. No. 6,127,418 discloses the use of pregabalin in treating gastrointestinal damage. PCT Publication WO98/58641 discloses use of pregabalin as an anti-inflammatory agent.

One significant problem of GABA analogs is the formation of toxic impurities such as the corresponding gamma-lactams during synthesis and/or formulation and/or storage. The amino group of GABA analogs reacts with its carboxyl functional group to form lactams. This autodegradation due to the intramolecular condensation between the amino and carboxyl group within the GABA analog molecule to form the corresponding lactam presents serious difficulties in formulating GABA analogs and needs to be minimized for safety reasons. GABA analogs under usual storage conditions and also in the presence of water tend to form the undesirable lactam side product. Many of the excipients that may be used for formulating preparations of GABA analogs tend to react with them with lapse of time to form the corresponding lactams by accelerating the dehydration reaction between the amino group and the carboxyl group within the GABA analog molecule. Further, reaction between a GABA analog and the formulation excipients is further accelerated with the use of water or an organic solvent in manufacturing of a pharmaceutical preparation. Such a degradation of GABA analogs with lapse of time due to the formation of the lactam is ascribed to its chemical structure and developed by the influence of water, irrespective of whether or not GABA analog is in the state of a solution or a solid. In the case of gabapentin, the intramolecular lactam 4-cyclohexylpyrrolidone is considered to be more toxic than gabapentin. The cyclic lactam of Pregabalin (4-isobutyl-pyrrolidin-2-one) is also an undesired side product. Hence controlling and monitoring lactam impurity during development and shelf life of pharmaceutical compositions of GABA analog is an important parameter.

Further, the primary amino-group present in the GABA molecule not only is able to form a lactam-ring but also to react with other reducing carbonyl functions. With excipients such as lactose, pregabalin is also known to form conjugates by undergoing a Maillard reaction. The product of this reaction is a simple glycosylamine, which are a combination of lactose and the amine of pregabalin after net loss of water. About seven degradants identified in formulated pregabalin were determined to be conjugates of pregabalin resulting from Maillard reactions (Reference). Further lactam formation is found to occur with these pregabalin conjugates.

It is therefore desirable to provide pharmaceutical compositions that do not comprise conjugate forming excipients, thereby being essentially free of such conjugates and ensuring stability under storage conditions.

Various attempts have been described in the art to reduce the tendency of GABA analogs to form the corresponding lactam in the bulk material and in final, unit dosage forms and provide stable formulations thereof. U.S. Pat. No. 6,054,482 relates to a method of preparing gabapentin that contains less than 20 ppm of an anion of a mineral acid. Pharmaceutical compositions described consist essentially of: (i) an active ingredient which is gabapentin in the free amino acid, crystalline anhydrous form containing less than 0.5% by weight of its corresponding lactam and less than 20 ppm of an anion of a mineral acid and (ii) one or more pharmaceutically acceptable adjuvants that do not promote conversion of more than 0.2% by weight of the gabapentin to its corresponding lactam form when stored at 25° C. and an atmospheric humidity of 50% for one year selected from the group consisting of hydroxypropylmethylcellulose, polyvinylpyrrolidone, crospovidone, poloxamer 407, poloxamer 188, sodium starch glycolate, copolyvidone, maize starch, cyclodextrine, lactose, talc and copolymers of dimethylamino-methacrylic acid and neutral methacrylic acid ester.

European Patent EP 1077692B1 describes the use of alpha-amino acid as stabilizer in pharmaceutical preparations containing a 4-amino-3-substituted-butanoic acid derivative such as gabapentin or pregabalin thereby preventing lactam formation due to autocondensation within the molecule. European Patent EP1077691B1 relates to formulations of 4-amino-3-substituted-butanoic acid derivative wherein degradation owing to lactam formation during formulation and storage is prevented by blocking the evaporation and movement of small amount of residual water in a solid composition by the use of a humectant as a stabilizer. PCT Publication WO2008/003285 discloses stabilized compositions of pregabalin comprising one or several auxiliary agents such as alkaline earth phosphates or pentites and/or hexites or a polyacrylate and being largely free from saccharides such as lactose and not requiring amino acids for stabilization. PCT Publication WO2005/051384 relates to the use of calcium carbonate as a stabilizing agent in solid pharmaceutical composition of an amino acid such as pregabalin or gabapentin. U.S. Pat. No. 6,488,964 relates to manufacturing coated particles of pregabalin, whose lactam content is less than 0.5% wherein a coating solution of polymethacrylate, aminoethyl methacrylate copolymers and cellulose polymers, alone or as a mixture, in at least one organic solvent is sprayed onto the said particles. U.S. Patent Application 2008/0058420A1 relates to a pharmaceutical composition comprising gabapentin and a mixture of excipients capable of not promoting the conversion of gabapentin into the corresponding lactam impurity, which comprises (i) a sliding agent selected from a calcium salt of weak acid, (ii) a lubricating agent selected from hydrogenated castor oil and glyceryl behenate; and optionally (iii) a diluting agent selected from a monosaccharidic sugar like sorbitol, xylitol, mannitol, fructose, dextrose and erythritol and polysaccharidic derivatives like saccharose, mannitol, isomalt, maltitol, a galactomannan, alginic acid or one of its salts, a pectin, a carageenan and maltodextrin. A composition of gabapentin based on use of three different groups of excipients has been disclosed, but that a specific set of excipients causes stabilization or reduction in conversion of gabapentin into the corresponding lactam impurity has not been discussed. The corresponding lactamic impurity in these compositions is said to not exceed 0.2% by weight of gabapentin after being maintained for 3 months at the storage conditions of 25° C. with 60% of relative humidity, and/or at 30° C. with 65% of relative humidity.

European Patent Application EP1395242A relates to liquid pharmaceutical composition comprising a GABA analog such as gabapentin or pregabalin and one or more polyhydric aliphatic alcohols containing 2 to 6 carbon atoms selected from the group consisting of: glycerol, xylitol, sorbitol, mannitol, and a mixture of glycerol and xylitol, with the composition having a pH of about 5.5 to about 7.0 and containing less than 0.5% by weight of gabapentin lactam or pregabalin lactam, respectively, after storage at 2° C. to 10° C. for 18 months to 2 years. One or more polyhydric alcohols comprise about 25% to about 75% weight/volume of the composition. European Patent Application EP1543831A relates to an aqueous pharmaceutical preparation for oral administration comprising pregabalin dissolved or dispersed in aqueous liquid containing suitable adjuvants, characterized in that the acidity of the pharmaceutical preparation is adjusted to a stable pH-range below 6.5 and above 5.5 and the liquid preparation is preserved by a combination of methyl- and ethyl-parabene in a w/v ratio of 3:1 to 5:1. PCT Publication WO2007/107835 relates to a stable oral liquid formulation comprising GABA analogue and polyhydric alcohol containing 2 to 6 carbon atoms, wherein the content of polyhydric alcohol containing 2 to 6 carbon atoms selected from glycerol, xylitol, sorbitol, mannitol and mixture thereof, is equal to or less than 20% weight/volume (w/v) of the composition. The composition is said to have less than 0.5% by weight of the corresponding lactam analogue after storage at about 2° C. to 10° C. for 18 months to 2 years.

In view of the aforesaid, it is necessary to provide pharmaceutical compositions of GABA analogs that are substantially free of any lactam impurities. Though some stabilized pharmaceutical compositions have been disclosed in the art, it is desirable to have compositions of GABA analogs that have excellent storage stability with very minimum lactam formation over the storage period. There further exists a need to have compositions that are not only stable but also have desirable in-vitro dissolution and bioavailability during storage. Further a need also exists to identify excipients that when used in pharmaceutical compositions of GABA analogs prevent or minimize degradation of GABA analogue to the corresponding lactam form.

The present inventors have surprisingly found that a GABA analogue, namely pregabalin, can be formulated in a stable pharmaceutical composition having low levels of—pregabalin lactam, with a disaccharide except for trehalose or higher polyol as a stabilizer. The present invention provides a stabilized pharmaceutical composition of pregabalin whose lactam content is less than about 0.2% by weight preferably less than about 0.15% by weight relative to the weight of pregabalin. The invention provides a process for manufacturing stabilized pharmaceutical compositions of pregabalin whose lactam content by weight relative to the weight of pregabalin is less than about 0.2% by weight, preferably less than about 0.15% by weight relative to the weight of pregabalin.

SUMMARY OF THE INVENTION

The present invention relates to stabilized pharmaceutical compositions of pregabalin. The invention relates to preventing the degradation of pregabalin in a pharmaceutical composition, by the use of a disaccharide or higher polyol except for trehalose. Further, the present invention provides compositions of pregabalin whose lactam content is less than about 0.2%, preferably less than about 0.15% by weight relative to the weight of pregabalin. The invention also relates to a process of preparation of such stabilized compositions.

DETAILED DESCRIPTION OF THE INVENTION

The present invention provides stabilized pharmaceutical compositions comprising a pregabalin and a disaccharide or higher polyol except for trehalose that are substantially free of any lactam impurity.

Further, the pregabalin may be used in the form of, but not limited to, salts, solvates, polymorphs, prodrugs, hydrates, or derivatives thereof.

The term "disaccharide or higher polyol" refers to hydrogenated disaccharide, oligosaccharide or polysaccharide or any derivatives thereof. One or more disaccharide polyols that may be employed in the compositions of the present invention include, but are not limited to, isomalt, hydrogenated maltulose, lactitol, maltitol, isomaltitol, or derivatives thereof. One or more higher oligosaccharide or polysaccharide polyols that may be employed in the compositions of the present invention include, but are not limited to, maltotriitol, maltotetraitol or other hydrogenated oligo- and polysaccharides obtained by hydrolysis of starch followed by a hydrogenation, cellobiitol, cellotriitol, xylobiitol, xylotriitol, inulotriitol or other hydrogenated oligo- and polysaccharides obtained by hydrolysis of cellulose, xylans or fructans such as for example inulin followed by hydrogenation. In one embodiment, the disaccharide polyol employed is isomalt, lactitol, maltitol, or enantiomers or derivatives thereof. In another embodiment, the disaccharide polyol employed is isomalt.

In conjunction with the present invention, isomalt is understood to refer to an almost equimolar mixture of the two stereoisomers 6-O-α-D-glucopyranosyl-D-sorbitol (1,6-GPS) and 1-O-α-D-glucopyranosyl-D-mannitol (1,1-GPM), which is also known by the brand name Palatinit®. Isomalt variants are also included within the meaning of the term "isomalt" and include mixtures containing 1,6-GPS and 1,1-GPM, which are characterized by quantity ratios of 1,6-GPM to 1,6-GPS, which differ from the quantity ratios of isomalt. Such mixtures are disclosed in U.S. Pat. No. 5,578,339, for example, which is thus included in the disclosure content of the present patent application with regard to the quantitative composition of sugar alcohol mixtures containing 1,1-GPM and 1,6-GPS and methods of producing the same. Therefore, the isomalt variants may be, for example, mixtures of 10 wt % to 50 wt % 1,6-GPS, 2 wt % to 20 wt % 1,1-GPS and 30 wt % to 70 wt % 1,1-GPM, or mixtures of 5 wt % to 10 wt % 1,6-GPS, 30 wt % to 40 wt % 1,1-GPS and 45 wt % to 60 wt % 1,1-GPM.

The term "lactam impurity" or "corresponding lactam" refers to undesired degradation product produced by an intramolecular condensation reaction of the γ-amino group and the carboxylic acid group of a GABA analog or any derivatives thereof. This cyclization product of the pregabalin is its corresponding lactam or lactam impurity.

The term "substantially free of any lactam impurity" refers to pregabalin composition of the present invention comprising not more than about 0.2% by weight, preferably not more than about 0.15% by weight, of lactam impurity relative to the weight of pregabalin.

The pregabalin is present in the compositions of the present invention in an amount of about 10% to about 99% by weight of the composition. According to the invention pregabalin is present in the pharmaceutical compositions of the present invention in an amount of about 10% to about 90% by weight of the composition. The stabilized pharmaceutical compositions of the present invention with up to 50 mg pregabalin, comprise preferably about 10% to about 60% by weight of pregabalin, more preferably about 20% to about 50% by weight of pregabalin, in particular 25% by weight of pregabalin based on total weight of the composition. The stabilized pharmaceutical compositions of the present invention with more than 50 mg pregabalin, comprise preferably about 40% to about 99% by weight of pregabalin, more preferably about 50% to about 85% by weight of pregabalin, in particular about 70% to about 80% by weight of pregabalin, based on the total weight of the composition.

The amount of disaccharide or higher polyol stabilizer present in the pharmaceutical compositions of the present invention is about 0.01% to about 75% by weight of the composition. In one embodiment the amount of disaccharide or higher polyol present in the pharmaceutical compositions of the present invention is about 0.01% to about 65% by weight of the composition. In another embodiment the amount of disaccharide or higher polyol present in the pharmaceutical compositions of the present invention is about 0.01% to about 50% by weight of the composition. According to the invention isomalt is present in an amount of about 0.01% to about 75% by weight of the composition. Further the ratio of pregabalin to stabilizer in the pharmaceutical compositions of the present invention may range from about 1:9 to about 9:1. In one embodiment of the invention ratio of pregabalin to isomalt may range from about 1:9 to about 9:1.

The term "composition" or "formulation" has been employed interchangeably for the purpose of the present invention and mean that it is a pharmaceutical composition which is suitable for administration to a patient. The stabilized pharmaceutical compositions of the present invention can be in the form of a solid or liquid dosage form.

The stabilized solid formulations of pregabalin of the present invention comprising disaccharide or higher polyol except for trehalose, are stable and substantially free of lactam impurity when compared to the marketed formulation. In one embodiment, stabilized solid compositions of pregabalin comprising disaccharide or higher polyol except for trehalose, surprisingly, are stable and substantially free of lactam impurity when compared to the marketed Lyrica® formulation of pregabalin. Without wishing to be bound by any theory, the highly desirable stability of the solid pharmaceutical compositions of the present invention that are substantially free of any lactam impurity is believed to be based on the fact that the disaccharide or higher polyol stabilizers with low hygroscopicity and non-reducing nature employed in the present invention are less likely to take up any moisture and act as protectants against contact of the GABA analog or formulation thereof with environmental moisture or the equilibrium moisture inherent in formulation. In this way, degradation of the GABA analog in such formulations is significantly reduced. Any moisture-induced degradation which includes cyclization, and even thermal dehydration, such as that initiated by compression and facilitated or catalyzed by moisture or dehydration due to ionic attractions which may be induced by moisture is significantly reduced with the use of stabilizers such as disaccharide or higher polyol except for trehalose in the pharmaceutical compositions of the present invention.

Further, without wishing to be bound by any theory, stabilizer such as isomalt that has low hygroscopicity and is heat stable, provides moisture stabilizing action thereby not accelerating any degradation reaction leading to autocondensation within the pregabalin molecule. Isomalt absorbs virtually no moisture at a temperature of 25° C. and relative humidities of up to 85% and being non-reducing does not contribute towards color development in the formulation due to Maillard reaction. Thus isomalt, is surprisingly found to behave as a stabilizer in the solid compositions comprising pregabalin. With the use of isomalt presence of degradation products in the formulation is substantially reduced and in particular, lactam formation is minimized. Use of isomalt or any disaccharide or higher polyol except for trehalose, also masks the bitter taste the GABA analog and thereby in addition to a stabilized composition also provides a taste-masked composition.

The fact that the use of isomalt or any disaccharide or higher polyol except for trehalose, which are suitable for stabilizing compositions containing pregabalin, is surprising because other compounds having similar chemical structures such as non-reducing mono-saccharides (e.g. xilitol, sorbitol, mannitol) and the trehalose cause an unacceptable change of the appearance and/or smell of these mixtures containing pregabalin with lapse of time.

The change of colour and smell of a pharmaceutical composition, even if the known impurities are under the required level, is unacceptable. The aggregation of particles can cause the change of the disintegration of the composition. These problems are also solved by using of isomalt or any disaccharide or higher polyol except for trehalose.

With the liquid compositions of the present invention, it was surprisingly found that disaccharide or higher polyols, can be used as stabilizers whereby formulations substantially free of any lactam impurity i.e. comprising not more than about 0.2% by weight, preferably not more than about 0.15% by weight of lactam impurity relative to the weight of pregabalin can be provided. The disaccharide or higher polyols have a stabilizing and preservative effect in the liquid compositions of the present invention.

The stabilized pharmaceutical compositions of the present invention may further comprise at least one pharmaceutically acceptable excipient. By "pharmaceutically acceptable excipient" is meant a material which is not biologically or otherwise undesirable, i.e., the material can be administered to an individual along with the drug and stabilizer in a formulation without causing any undesirable biological effects or interacting in a deleterious manner with any of the components of the formulation in which it is contained. Only pharmaceutical acceptable excipients which do not contain a reactive aldehyde or keto functionality are used, since these functionalities react with the active components.

The pharmaceutically acceptable excipients that may be present in the stabilized pharmaceutical compositions of the present invention include, but are not limited to, diluents, binders, disintegrants, lubricants, colorants, flavors, pH adjusters, viscolizers, artificial and natural sweeteners, and the like. Diluents that may optionally be incorporated in the compositions of the present invention include, but are not limited to, talc, sucrose, microcrystalline cellulose, dibasic calcium phosphate, starch, maize starch, pregelatinized starch, partially pregelatinized starch and the like, and combinations thereof. Binders employed in the compositions of the present invention include, but are not limited to, microcrystalline cellulose, polyethylene glycol, polyvinylpyrrolidone, maize starch, pregelatinized starch, partially pregelatinized starch, hydroxypropyl methylcellulose, hydroxypropyl cellulose and the like, or combinations thereof. Disintegrants employed in the compositions of the present invention include, but are not limited to, sodium starch glycolate, sodium carboxymethyl cellulose, croscarmellose sodium, crospovidone, polyvinylpyrrolidone, methyl cellulose, starch, pregelatinized starch, partially pregelatinized starch and the like or combinations thereof. Lubricants that may be employed in the compositions of the present invention include, but are not limited to, magnesium stearate, calcium stearate, zince stearate, sodium stearyl fumarate and the like, or combinations thereof.

The stabilized solid pharmaceutical composition of pregabalin according to the invention is present in the form of, but not limiting to, capsules, tablets, granules, pellets, powders, lozenges, multiparticulates and the like. The pharmaceutical composition according to the invention is present in the form of a dispersible tablet, a dry powder or granules for reconstitution. In one embodiment, capsules of the present invention can be, but not limiting to, immediate release or modified release types. In another embodiment, tablets of the present invention can be, but not limiting to, immediate release or modified release types or orally disintegrating types.

In a further embodiment the pharmaceutical compositions of the present invention can be in the form of a stabilized liquid formulation of pregabalin. Liquid form preparations include solutions, syrups, suspensions and emulsions, for example, with water or certain glycol solutions. For parenteral injections, liquid preparations can be formulated in solution in aqueous polyethylene glycol solutions.

The present invention also provides a process for the preparation of a stabilized pharmaceutical composition comprising a pregabalin. Such a process comprises combining the pregabalin with a disaccharide or higher polyol as a stabilizer and, if necessary a pharmaceutically acceptable excipient. In one embodiment the disaccharide or higher polyol stabilizer is isomalt. Further the invention relates to a process for the preparation of a stabilized pharmaceutical preparation comprising pregabalin which is in solid or liquid form. In one embodiment, the stabilized solid compositions of the present invention can be prepared by dry blending the active and stabilizer along with other pharmaceutically acceptable excipients followed by encapsulating in hard capsules. In another embodiment granules of pregabalin may be prepared for e.g. for filling into capsules or compressing in the form of tablets by any granulation method known to a person skilled in the art, including but not limited to, dry granulation, wet granulation, melt granulation and the like, without leading to the formation of corresponding lactam form of the pregabalin, such that the formulation provided is substantially free of any lactam impurity and is stable. In another embodiment, granules, pellets and the like of stabilizer or other pharmaceutically acceptable excipients may be prepared and used to formulate stabilized pharmaceutical compositions of the present invention. The powders, granules or tablets and the like of pregabalin may optionally be surface-coated. The surface-coating may be a aesthetic or functional coat. Surface-coating may be carried out by a well-known method using a fluidized bed or a rotary pan. A film-forming material such as, but not limited to, a cellulose derivative, e.g., hydroxypropylcellulose (HPC), hydroxypropylmethylcellulose (HPMC), etc., a polyvinyl pyrrolidone, Kollidon-VA64, Eudragits and the like may be employed for surface coating.

In a further embodiment is provided the use of stabilized pharmaceutical compositions of pregabalin of the present invention for the manufacture of a medicament for the treatment of epilepsy, faintness attacks, hypokinesia, cranial traumas, neurodegenerative disorders such as Alzheimer's disease, Huntington's chorea or Parkinson's disease and amyotrophic lateral sclerosis, depression, mania and bipolar disorders, anxiety, panic inflammation, renal colic, insomnia, gastrointestinal damage, incontinence, pain including neuropathic pain, muscular pain, skeletal pain and migraine. Further, the present invention provides a method of treating epilepsy, faintness attacks, hypokinesia, cranial traumas, neurodegenerative disorders such as Alzheimer's disease, Huntington's chorea or Parkinson's disease and amyotrophic lateral sclerosis, depression, mania and bipolar disorders, anxiety, panic inflammation, renal colic, insomnia, gastrointestinal damage, incontinence, pain including neuropathic pain, muscular pain, skeletal pain and migraine, comprising administering to the subject in need thereof stabilized pharmaceutical compositions of the present invention.

While the present invention has been described in terms of its specific embodiments, certain modifications and equivalents will be apparent to those skilled in the art and are intended to be included within the scope of the present invention. The invention is further illustrated by the following examples, which are for illustrative purposes and should not be construed as limiting the scope of the invention in any way.

EXAMPLES

Example 1/A

Comparative Evaluation of Stability of Pregabalin with Various Excipients

A preformulation study was carried out to evaluate the effect various physically admixed excipients had on stability of pregabalin. The percent lactam content in the preformulation admixture was determined by HPLC.

| S.No. | Name of components | Condition Time Point | % Known Impurities Lactum RRT = 3.91 |
|---|---|---|---|
| 1. | Pregabalin | Initial | <0.0003 |
|  |  | 60° C./2 Weeks/closed | 0.006 |
|  |  | 40° C./75% RH/4 Weeks/open | 0.004 |
| 2. | Pregabalin + Lactose monohydrate (Supertab 30GR) (1:3) | Initial | <0.0003 |
|  |  | 60° C./2 Weeks/closed | 0.017 |
|  |  | 40° C./75% RH/4 Weeks/open | 0.004 |
| 3. | Pregabalin + Talc (1:0.5) | Initial | <0.0003 |
|  |  | 60° C./2 Weeks/closed | 0.031 |
|  |  | 40° C./75% RH/4 Weeks/closed | 0.006 |
|  |  | 40° C./75% RH/4 Weeks/open | 0.008 |

-continued

| S.No. | Name of components | Condition Time Point | % Known Impurities Lactum RRT = 3.91 |
|---|---|---|---|
| 4. | Pregabalin + Colloidal silicon dioxide (Aerosil 200P) (1:0.25) | Initial<br>60° C./2 Weeks/closed<br>40° C./75% RH/4 Weeks/open | 0.002<br>0.68<br>0.16 |
| 5. | Pregabalin + Isomalt (galenIQ960) (1:3) | Initial<br>60° C./2 Weeks/closed<br>40° C./75% RH/4 Weeks/closed<br>40° C./75% RH/4 Weeks/open | 0.003<br>0.009<br>0.001<br>0.001 |
| 6. | Lyrica capsule powder (50 mg) (comprising active, lactose monohydrate, corn starch and talc) | Initial<br>60° C./2 Weeks/closed<br>40° C./75% RH/4 Weeks/open | 0.020<br>0.145<br>0.043 |
| 7. | Lyrica capsule powder (300 mg) (comprising active, lactose monohydrate, corn starch and talc) | Initial<br>60° C./2 Weeks/closed<br>40° C./75% RH/4 Weeks/open | 0.012<br>0.068<br>0.014 |

The above table shows that the active pregabalin could be prevented from degradation to lactam form with lapse of time by the use of isomalt. From the above data it is evident that lactam formation is considerably low in the preformulation admixture of pregabalin and isomalt, as compared to the marketed formulation LYRICA®.

Example 1/B

Comparative Evaluation of Stability of Pregabalin with Non-Reducing Saccharides

A preformulation study was carried out to evaluate the effect of various physically admixed non-reducing saccharides on the stability of pregabalin.

| S.No. | Name of components | Condition Time Point | Appearance | Scent |
|---|---|---|---|---|
| P-0. | Pregabalin | Initial | White crystalline powder | Odourless |
| | | 50° C./4 Weeks/closed | White crystalline powder | Odourless |
| | | 40° C./75% RH/4 Weeks/open | White crystalline powder | Odourless |
| P-1. | Pregabalin + Isomalt (GaleniQ 960) (1:1) | Initial | White crystalline powder | Odourless |
| | | 50° C./4 Weeks/closed | White crystalline powder | Odourless |
| | | 40° C./75% RH/4 Weeks/open | White crystalline powder | Odourless |
| P-2. | Pregabalin + Trehalose (1:1) | Initial | White crystalline powder | Sweet |
| | | 50° C./4 Weeks/closed | Yellowish crystalline powder | Sourish |
| | | 40° C./75% RH/4 Weeks/open | Aggregated, white crystalline powder | Odourless |
| P-3. | Pregabalin + Xilitol (1:1) | Initial | White crystalline powder | Odourless |
| | | 50° C./4 Weeks/closed | Yellowish crystalline powder | Lightly sweet |
| | | 40° C./75% RH/4 Weeks/open | Yellowish, wet crystalline powder | Odourless |
| P-4. | Pregabalin + Sorbitol (1:1) | Initial | White, crystalline powder | Odourless |
| | | 50° C./4 Weeks/closed | White, crystalline powder | Odourless |
| | | 40° C./75% RH/4 Weeks/open | Greyish-white, strongly aggregated crystals | Odourless |
| P-5. | Pregabalin + Mannitol (1:1) | Initial | White, crystalline powder | Odourless |
| | | 50° C./4 Weeks/closed | White, crystalline powder | Odourless |
| | | 40° C./75% RH/4 Weeks/open | White, aggregated crystals | Odourless |

Example 2

Formulation of Pregabalin Capsules with 25% Drug Content (1473-050-25)

| Ingredients | mg/capsule |
|---|---|
| Pregabalin | 25 |
| Isomalt | 35 |
| Partially pregelatinized starch, USP | 35 |
| Talc, USP | 5 |
| Total weight | 100 |

Pregabalin and all excipients other than talc were sifted and blended. To this blend, sifted talc was added and further blended. This drug-excipient blend was filled in capsules using a manual capsule filling machine.

In Vitro Dissolution Study

In vitro dissolution study was carried out for pregabalin capsules of the present example and the marketed Lyrica® capsules using USP type II apparatus in 900 ml of 0.1N HCl at 50 rpm. The comparative dissolution profile is as tabulated beneath:

|  | % Drug release | | | |
| --- | --- | --- | --- | --- |
|  | Lyrica ® 25 mg | | Pregabalin capsules of the present example | |
| Time (mins) | Initial | 1M 40° C./75% RH | Initial | 1M 40° C./75% RH |
| 5 | 78.5 | 70.7 | 97.3 | 98.0 |
| 10 | 96.4 | 91.2 | 101.1 | 103.0 |
| 15 | 98.5 | 96.3 | 100.8 | 103.4 |
| 30 | 100.7 | 102.1 | 101.2 | 103.7 |

Assay

The assay of pregabalin for capsules of the present example was performed and compared against the marketed Lyrica® formulation, the results of which are as shown beneath:

| Formulation | Initial | 1M 40° C./75% RH |
| --- | --- | --- |
| LYRICA 25 mg | 102.9 | 99.2 |
| Pregabalin capsules of the present example | 101.1 | 104.7 |

Stability Studies

Comparative evaluation of related substances of pregabalin capsules discussed in this example and the marketed Lyrica® capsules 25 mg was carried out, results for which are as tabulated beneath.

|  |  | % Known impurities LAC RRT- 3.91 1M | |
| --- | --- | --- | --- |
| Pack | Conditions | Pregabalin capsules of present example | LYRICA ® 25 mg |
| — | Initial | <0.0003 | 0.016 |
| Glass vial | 60° C./2W/closed | 0.03 | 0.161 |
| Glass vial | 4 Weeks open 40° C./75% RH | 0.008 | 0.044 |
| PVC/ALU blister | 1M PVC/Alu 40° C./75% RH | 0.006 | 0.041 |

Thus the data indicates that use of isomalt in the pregabalin compositions of the present invention effectively stabilizes them. One month stability data in PVC/Alu blister at 40° C./75% relative humidity shows lactam levels considerably below 0.05% by weight relative to the weight of GABA analog.

Example 3

Formulation of Pregabalin Capsules with 25% Drug Content (1573-093-25)

| Ingredients | mg/capsule |
| --- | --- |
| Pregabalin | 25 |
| Isomalt | 51 |
| Maize starch, USP | 5 |
| Talc, USP | 19 |
| Total weight | 100 |

In Vitro Dissolution Study

In vitro dissolution study was carried out for pregabalin capsules of the present example and the marketed Lyrica® capsules using USP type II apparatus in 900 ml of 0.1N HCl at 50 rpm. The comparative dissolution profile is as tabulated beneath:

|  | % Drug release | | | |
| --- | --- | --- | --- | --- |
|  | Lyrica ® capsules 25 mg | | Capsules of the present invention | |
| Time (mins) | Initial | 1M 40° C./75% RH | Initial | 1 M 40° C./75% RH |
| 5 | 78.5 | 70.7 | 60.3 | 64.2 |
| 10 | 96.4 | 91.2 | 89.9 | 95.1 |
| 15 | 98.5 | 96.3 | 93.8 | 100.1 |
| 30 | 100.7 | 102.1 | 95.9 | 102.5 |

Assay

The assay of pregabalin for capsules of the present example was performed and compared against the marketed Lyrica® formulation, the results of which are as shown beneath:

| Formulation | Initial | 1M 40° C./75% RH |
| --- | --- | --- |
| LYRICA 25 mg | 102.9 | 99.2 |
| Pregabalin capsules of the present invention | 102.6 | 103.7 |

Stability Studies

Comparative evaluation of related substances of pregabalin capsules discussed in this example and the marketed Lyrica® capsules 25 mg was carried out, results for which are as tabulated beneath.

|  |  | % Known impurities LAC RRT-3.91 1M | |
| --- | --- | --- | --- |
| Pack | Conditions | Pregabalin capsules of present invention | LYRICA ® 25 mg |
| — | Initial | 0.001 | 0.016 |
| Glass vial | 60° C./2W/closed | 0.026 | 0.161 |
| PVC/ALU blister | 1M PVC/Alu 40° C./75% RH | 0.008 | 0.041 |

Thus the data indicates that use of isomalt in the pregabalin compositions of the present invention effectively stabilizes them. One month stability data in PVC/Alu blister at 40° C./75% relative humidity shows lactam levels considerably below 0.05% by weight relative to the weight of GABA analog.

Example 4

Formulation of Pregabalin Capsules with 25% Drug Content (1537-035-25)

| Ingredients | mg/capsule |
| --- | --- |
| Pregabalin | 25 |
| Isomalt | 45 |

-continued

| Ingredients | mg/capsule |
|---|---|
| Maize starch | 11 |
| Talc | 19 |
| Total weight | 100 |

The capsules were prepared as per the procedure described in Example 2.

Example 5

Formulation of Pregabalin Capsules with 75% Drug Content (1537-047-300)

| Ingredients | mg/capsule |
|---|---|
| Pregabalin | 300 |
| Isomalt | 68 |
| Talc, USP | 32 |
| Total | 400 |

The capsules were prepared as per the procedure described in Example 2.

What we claim is:

1. A stabilized solid pharmaceutical composition, in powder form as a capsule filled with powder or as a tablet, suitable for oral administration, consisting of about 10% to about 99% by weight pregabalin and about 0.01% to about 75% by weight isomalt as stabilizer in an amount effective to stabilize the pregabalin against lactam formation, and optionally a pharmaceutically acceptable inert carrier.

2. The stabilized solid pharmaceutical composition for treating pain defined in claim 1 wherein pregabalin and isomalt are present in a weight ratio of 4.4:1 to 1:3.

3. A method of treating or preventing pain which comprises the step of orally administering to a patient in need of said treatment, a therapeutically effective amount of the stabilized solid pharmaceutical composition defined in claim 1.

4. The stabilized solid pharmaceutical composition defined in claim 1 wherein pregabalin and isomalt are present in a weight ratio of 1:3.

* * * * *